(12) United States Patent
Cardin et al.

(10) Patent No.: US 10,143,599 B2
(45) Date of Patent: Dec. 4, 2018

(54) RESILIENT ABSORBENT PRODUCTS WITH ENHANCED RESISTANCE TO TEARING

(71) Applicant: FEMPRO CONSUMER PRODUCTS ULC, Vancouver (CA)

(72) Inventors: Jeannine Cardin, St-Eugène de Grantham (CA); Mélanie Farley, Drummondville (CA); Helmut Georgi, Drummondville (CA)

(73) Assignee: Fempro Consumer Products ULC, Vancouver (CA)

( * ) Notice: Subject to any disclaimer, the term of this patent is extended or adjusted under 35 U.S.C. 154(b) by 0 days.

(21) Appl. No.: 14/526,006

(22) Filed: Oct. 28, 2014

(65) Prior Publication Data

US 2015/0133883 A1 May 14, 2015

Related U.S. Application Data

(60) Provisional application No. 61/897,017, filed on Oct. 29, 2013, provisional application No. 61/897,312, filed on Oct. 30, 2013, provisional application No. 61/900,640, filed on Nov. 6, 2013.

(51) Int. Cl.
*A61F 13/47* (2006.01)
*A61F 13/15* (2006.01)
*A61F 13/534* (2006.01)
*A61F 13/53* (2006.01)

(52) U.S. Cl.
CPC .... *A61F 13/4702* (2013.01); *A61F 13/15203* (2013.01); *A61F 13/4704* (2013.01); *A61F 13/534* (2013.01); *A61F 2013/15292* (2013.01); *A61F 2013/15373* (2013.01); *A61F 2013/15463* (2013.01); *A61F 2013/16* (2013.01); *A61F 2013/530233* (2013.01); *A61F 2013/530547* (2013.01); *A61F 2013/530817* (2013.01)

(58) Field of Classification Search
CPC ............ A61F 13/15203; A61F 13/4702; A61F 2013/15292; A61F 2013/15373; A61F 2013/15406; A61F 2013/15463; A61F 2013/15471; A61F 2013/530226; A61F 2013/530233; A61F 2013/530481; A61F 2013/53051; A61F 2013/530547; A61F 2013/530554; A61F 2013/530817
See application file for complete search history.

(56) References Cited

U.S. PATENT DOCUMENTS

| 5,466,513 | A | * | 11/1995 | Wanek | A61F 13/53747 428/218 |
| 5,624,423 | A | * | 4/1997 | Anjur | A61F 13/47227 604/369 |
| 5,797,894 | A | * | 8/1998 | Cadieux | A61F 13/15203 604/378 |
| 7,488,310 | B2 | * | 2/2009 | Yang | A61F 13/15203 604/355 |

(Continued)

*Primary Examiner* — Lynne Anderson
(74) *Attorney, Agent, or Firm* — Amster, Rothstein & Ebenstein LLP (57) ABSTRACT

The present disclosure provides a sanitary napkin that is thin, highly absorbent and has resiliency properties that are selected to provide good comfort potential and at the same time reduce the likelihood of deformation and breaking. In a specific example, the sanitary napkin comprises a cover layer, an absorbent system and a barrier layer. The absorbent system includes an absorbent core and a reinforcement layer.

23 Claims, 6 Drawing Sheets (56) References Cited

U.S. PATENT DOCUMENTS

| | | |
|---|---|---|
| 8,211,078 B2 | 7/2012 | Noel |
| 2006/0047257 A1* | 3/2006 | Raidel .................. A61F 13/532 604/383 |
| 2007/0135787 A1* | 6/2007 | Raidel ............... A61F 13/15707 604/383 |
| 2014/0295135 A1 | 10/2014 | Thompson, Jr. et al. |
| 2014/0316363 A1* | 10/2014 | You ...................... A61F 13/472 604/375 |

* cited by examiner

RESILIENT ABSORBENT PRODUCTS WITH ENHANCED RESISTANCE TO TEARING

CROSS-RELATED APPLICATIONS

This application claims the benefit of U.S. 61/900,640, filed Nov. 6, 2013, U.S. 61/897,312, filed Oct. 30, 2013, and U.S. 61/897,017, filed Oct. 29, 2013. The contents of each of these documents are hereby incorporated by reference in their entirety.

FIELD OF TECHNOLOGY

The present disclosure relates to the art of fluid absorption and more particularly to disposable absorbent products for absorbing body fluids, more particularly to disposable absorbent products such as sanitary napkins, pantiliners and the like.

BACKGROUND INFORMATION

The sanitary protection industry has developed thin and flexible absorbent products that retain high absorption capacity. However, absorbent products that are thin and highly flexible when in place in undergarment of a user undergo deformation due to movement and compression of the wearer's thighs. These absorbent products do not readily return to their original conformation upon release of the compression force and remain more or less in their deformed conformation (i.e., resulting in bunching of the absorbent product). An absorbent product such as a sanitary napkin or a pantiliner that is deformed (that undergoes bunching) reduces its fluid absorption area, thereby increasing the incidence of failure rates.

To address these drawbacks, the industry has modified the stiffness of the absorbent core of the absorbent product. Particularly, the absorbent core of the absorbent product has been modified to include zones of varying stiffness, wherein the stiffness of the absorbent core has been increased in areas of the product that are more prone to displacements, such as for example, between the tights of the wearer, and the stiffness has been decreased in areas that are less prone to displacement, such as for example at the front and rear portions of the product. An example of sanitary napkin with zones of varying stiffness is discussed in U.S. Pat. No. 8,211,078, incorporated herein by reference in its entirety.

One potential difficulty with absorbent products having zones of varying stiffness is that while the product is less prone to deformation/bunching and more easily returns to its original configuration upon deformation, the product is more susceptible to tearing and breaking.

Against this background, it can be seen that there exists in the industry a need to provide absorbent products that have high resiliency and flexibility without loss of resistance or comfort for the wearer while maintaining high absorption capacities.

SUMMARY OF EMBODIMENTS

Various aspects of the present disclosure relate to a sanitary napkin comprising: a cover layer; a barrier layer joined to the cover layer; and a main body comprising an absorbent system, the absorbent system being disposed between the cover layer and the barrier layer, wherein the absorbent system comprises: an absorbent core having an inner side and an outer side; and a reinforcement layer apposed to the inner side of the absorbent core; wherein the sanitary napkin has a resiliency factor of at least about 15, a longitudinal tensile resistance of at least about 5250 cN and a transversal tensile resistance of at least about 3750 cN.

Various aspects of the present disclosure relate to a sanitary napkin comprising: a cover layer; a barrier layer joined to the cover layer; and a main body having a width and a length, the main body comprising an absorbent system disposed between the cover layer and the barrier layer, wherein the absorbent system comprises: an absorbent core having an inner side and an outer side; and a reinforcement layer apposed to the inner side of the absorbent core; wherein the sanitary napkin has a resiliency factor of at least about 15, a longitudinal tensile resistance of at least about 5250 cN and a transversal tensile resistance of at least about 3750 cN; and wherein the width of the main body is constant over at least 80% of the length of the main body.

Various aspects of the present disclosure relate to a sanitary napkin comprising: a cover layer; a barrier layer joined to the cover layer; and a main body comprising an absorbent system, the absorbent system being disposed between the cover layer and the barrier layer, wherein the absorbent system comprises: an absorbent core having an inner side and an outer side; and a reinforcement layer apposed to the inner side of the absorbent core; wherein the sanitary napkin has a resiliency factor of at least about 15, a longitudinal tensile resistance of at least about 3150 cN and a transversal tensile resistance of at least about 1450 cN.

Other aspects and features of the present disclosure will become apparent to those ordinarily skilled in the art upon review of the following description of specific embodiments in conjunction with the accompanying drawings.

BRIEF DESCRIPTION OF THE DRAWINGS

All features of embodiments which are described in this disclosure and are not mutually exclusive can be combined with one another. Elements of one embodiment can be utilized in the other embodiments without further mention. A detailed description of specific embodiments is provided herein below with reference to the accompanying drawings in which.

In the drawings, embodiments are illustrated by way of example. It is to be expressly understood that the description and drawings are only for the purpose of illustrating certain embodiments and are an aid for understanding. The scope of the claims should not be limited by the embodiments set forth in the present disclosure, but should be given the broadest interpretation consistent with the description as a whole.

DETAILED DESCRIPTION OF EMBODIMENTS

Specific examples of an absorbent product according to the present disclosure will now be described to illustrate the manner in which the principles of the present disclosure may be put into practice.

Figure 1:
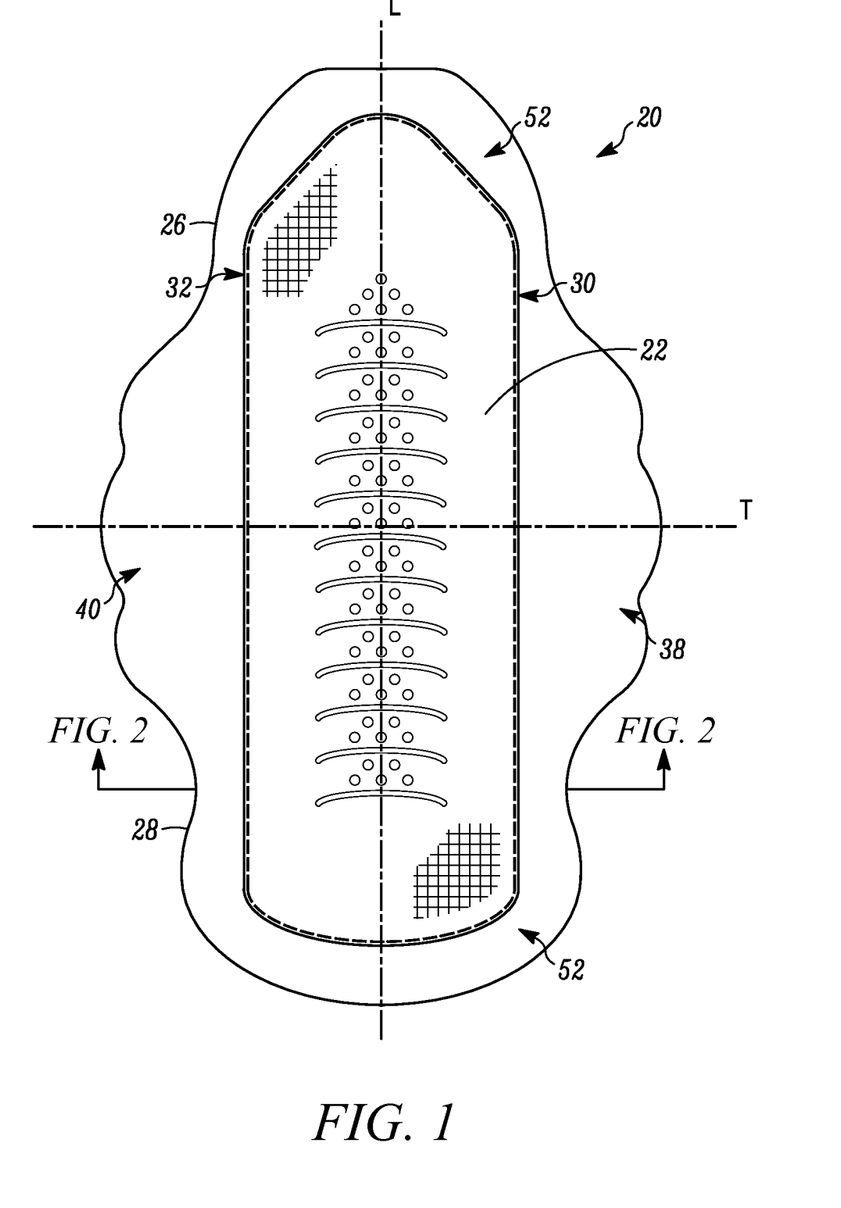
FIG. 1 is a top elevational view of the body-facing surface of a sanitary napkin in accordance with a non-limiting embodiment of the present disclosure.

FIG. 1 shows sanitary napkin 20 which is a non-limiting embodiment of a disposable absorbent product in accordance with the present disclosure. Alternatively, the disposable absorbent product may be a pantiliner.

The sanitary napkin 20 has a longitudinal axis L bisecting the sanitary napkin 20 in two identical longitudinal halves. Sanitary napkin 20 has a transversal axis T perpendicular to the longitudinal axis L and intersecting the longitudinal axis L at a central point on the sanitary napkin 20.

The sanitary napkin 20 has a main body 22 with a first transverse side defining a front portion 26 thereof and a second transverse side defining a rear portion thereof 28. Each of these sides is arcuate or is of any other suitable shape.

The main body 22 also has two longitudinal sides, a longitudinal side 30 and a longitudinal side 32. In some specific examples, the sanitary napkin 20 has a thickness of up to about 5.0 mm. For example, a thickness of up to about 3.5 mm, of up to about 3.0 mm, or any thickness value between about 2.0 mm and about 2.5 mm, or between about 1.5 mm and about 2.0 mm.

The sanitary napkin 20 comprises "flaps" or "wings" 38 and 40 that project laterally outward from each of the longitudinal sides 30 and 32. The flaps 38 and 40 may be of different forms and shapes as is known in the art.

The transverse axis T simultaneously bisects the flaps 38, 40.

In some implementations of this embodiment, the sanitary napkin 20 is provided without "flaps" 38 and 40.

Figure 2:
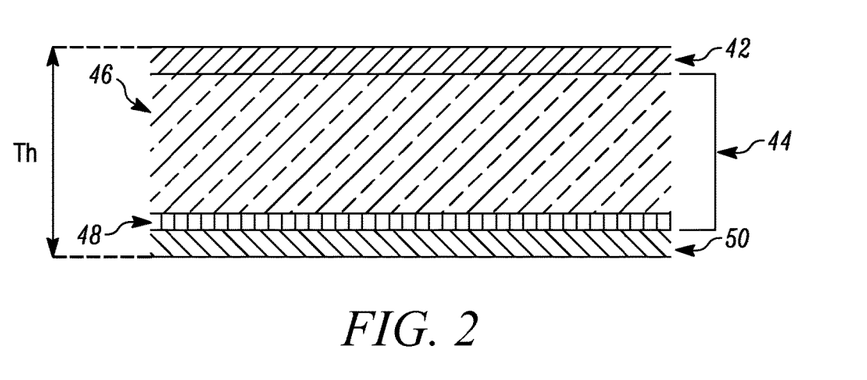
FIG. 2 is a cross-sectional view taken along the longitudinal axis of the sanitary napkin shown in FIG. 1.

As depicted in FIG. 2, the main body 22 is of laminate construction and preferably comprises a fluid-permeable cover layer 42 (also referred to as "topsheet"), an absorbent system 44, and a fluid-impervious barrier layer 50 (also referred to as "backsheet"). The absorbent system 44 has preferably at least two components, namely an absorbent layer 46 (also referred to as "absorbent core") and a reinforcement layer 48.

Each of the cover layer 42, absorbent system 44 including the absorbent layer 46 and the reinforcement layer 48, and the barrier layer 50 have an inner side facing the undergarment of the user (also referred to herein as the "garment-facing surface") and an outer side facing the body of the wearer (also referred to herein as the "body-facing surface"). As such, the sanitary napkin also has a body-facing surface which corresponds to the body-facing surface of the cover layer 42 and a garment-facing surface which corresponds to the garment-facing surface of the barrier layer 50.

As shown in FIG. 1, the absorbent system 44 is symmetric about a transverse centerline T along at least a portion of the absorbent system 44 which is adjacent to the transverse line T and is asymmetric about the transverse line at the front and rear portions of the absorbent system 43 (i.e., front portion 26 has a perimeter that has a different shape than the shape of the perimeter of the rear portion 28).

Figure 4:
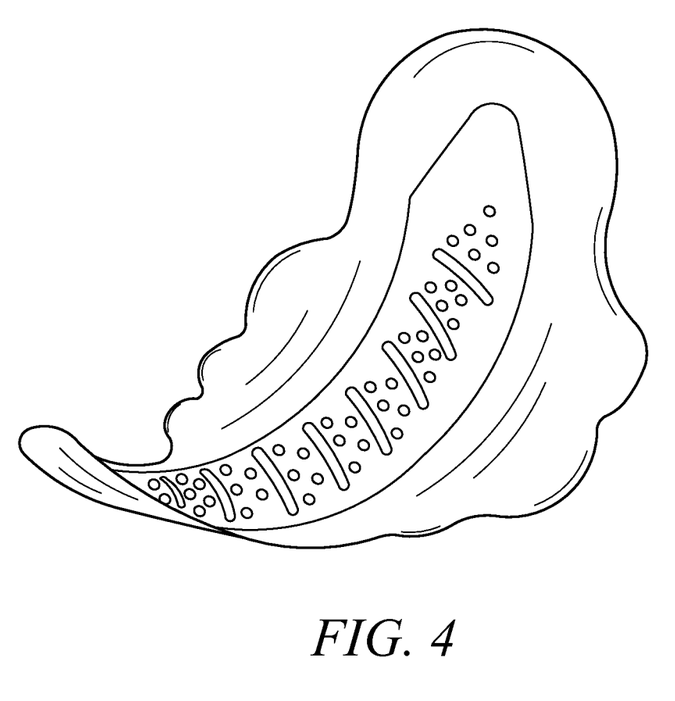
FIG. 4 is a perspective view of the sanitary napkin of FIG. 1, depicted in a position attained when the sanitary napkin is placed in the undergarment of a wearer.

The sanitary napkin 20 adopts a crotch conformation as shown in FIG. 4 when the sanitary napkin is placed in the undergarment of a wearer.

Figure 5:
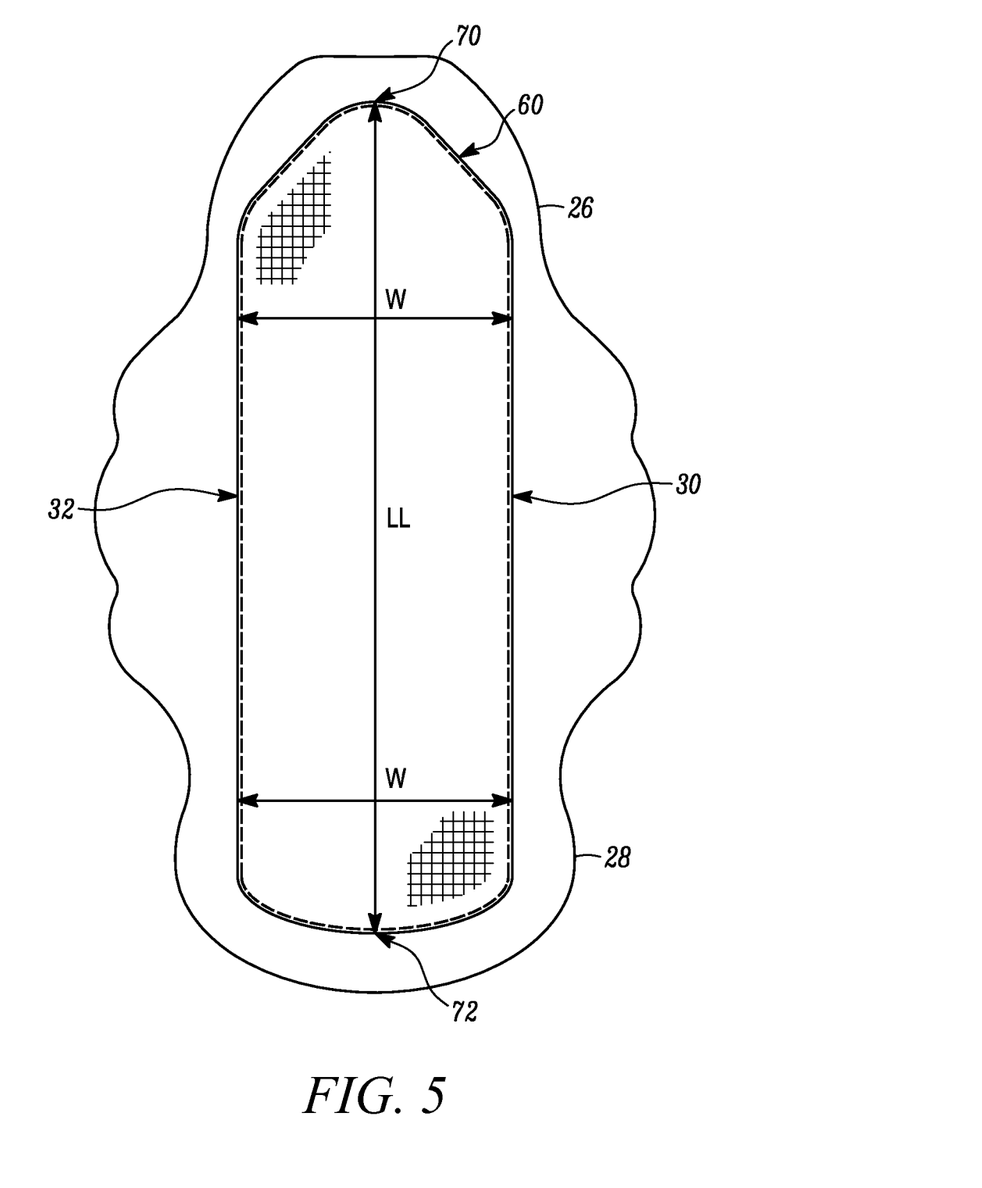
FIG. 5 is a top elevational view of the body-facing surface of the sanitary napkin of FIG. 1.

The main body 22 has a longitudinal length (LL) which is measured from the front apex 70 of the main body 22 to the rear apex 72 of the main body 22 (FIG. 5).

In a specific implementation, the width W of the main body 22, which is calculated from the longitudinal side 30 to the longitudinal side 32 of the main body 22, remains constant throughout a major portion of the main body 22 along the longitudinal length as can be seen in FIG. 5. In a specific implementation, the width W of the main body 22 is constant over at least 80% of the length of the main body. In another specific implementation, the width W of the main body 22 is constant over at least 81% of the length of the main body. In another specific implementation, the width W of the main body 22 is constant over at least 82% of the length of the main body. In another specific implementation, the width W of the main body 22 is constant over at least 83% of the length of the main body. In another specific implementation, the width W of the main body 22 is constant over at least 84% of the length of the main body. In another specific implementation, the width W of the main body 22 is constant over at least 85% of the length of the main body. In another specific implementation, the width W of the main body 22 is constant over at least 86% of the length of the main body.

The front portion 26 of the main body 22 is of narrowing width W forming a concave perimeter 60 along the front portion. In a specific implementation, the concave perimeter 60 is at least about 17.0% of the total perimeter of the main body 22. In a specific implementation, the concave perimeter 60 is at least about 18.0% of the total perimeter of the main body 22. In a specific implementation, the concave perimeter 60 is at least about 19.0% of the total perimeter of the main body 22.

In a specific implementation, the thickness Th of the main body 22 is substantially the same throughout.

Each of these layers is described hereinbelow in further detail.

Main Body—Cover Layer

The cover layer 42 may have various optional characteristics, as is known in the art. For example, the cover layer 42 may be a relatively low density, bulky, high-loft non-woven web material. The cover layer 42 may be composed of only one type of fiber, such as polyester or polypropylene or it may be composed of bi-component or conjugate fibers having a low melting point component and a high melting point component.

The fibers may be selected from a variety of natural and synthetic materials such as nylon, polyester, rayon (in combination with other fibers), cotton, acrylic fiber and the like and combinations thereof. In some implementations, the cover layer 42 of the sanitary napkin 20 includes polyethylene or polypeopylene or a combination of both. In a specific example, the cover layer 42 is a through-air bonded bicomponent of polyethylene/polypropylene sheet/core nonwoven.

Bi-component fibers may be made up of a polyester core and a polyethylene sheath. The use of appropriate bi-component materials may result in a fusible non-woven fabric and may also improve softness.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and to transport it away from the body and the point of deposition. Advantageously, the fibers which make up the cover layer 42 should not lose their physical properties when they are wetted, in other words they should not disintegrate, collapse or lose their resiliency when subjected to water or body fluid. The cover layer 42 may be treated to allow fluid to pass through it readily. The cover layer 42 also functions to transfer the fluid quickly to the absorbent system 44.

In a specific implementation, the cover layer 42 is hydrophobic and perforated.

When composed of synthetic hydrophobic fibers, the cover layer 42 may be treated with a surfactant to impart the desired degree of wettability.

The cover layer 42 may also be made of polymer film having large pores. Because of such high porosity, the film accomplishes the function of quickly transferring body fluid to the inner layers of the absorbent system.

In a specific example, the cover layer 42 is perforated to create channels so as to keep the skin of the wearer dry.

The cover layer 42 may be embossed to the absorbent system 44 in order to aid in promoting fluid transport by fusing the cover to the next layer. Such fusion may be effected locally, at a plurality of sites or over the entire contact surface of cover layer 42 with the absorbent system 44. Alternatively, the cover layer 42 may be attached to the absorbent system 44 by other means such as by adhesive.

Main Body—Absorbent System—Absorbent Core

Adjacent to the cover layer 42 on its garment-facing surface is the absorbent core 46 of the absorbent system 44. The absorbent core 46 provides the means of receiving body fluid from the cover layer 42 and for holding it.

The absorbent core 46 is, preferably, more dense than and has a larger proportion of smaller pores than the cover layer 42. These attributes allow the absorbent core 46 to contain body fluid and hold it away from the outer side of the cover layer 42, thereby preventing the fluid from re-wetting the cover layer 42 and its surface.

Figure 3A:
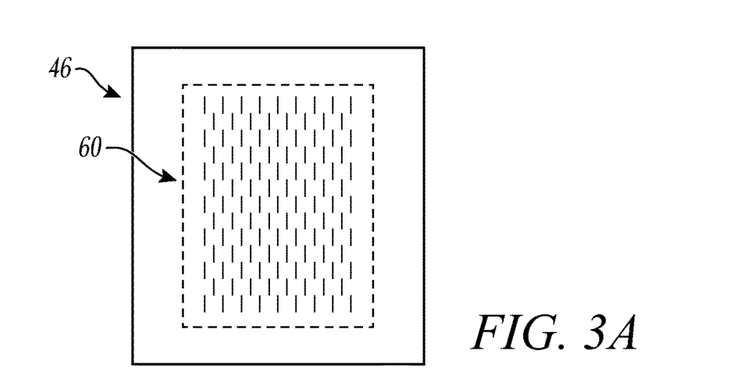
FIG. 3A is top elevational view of the body-facing surface of at least a portion of the absorbent core of FIG. 2.
Figure 3B:
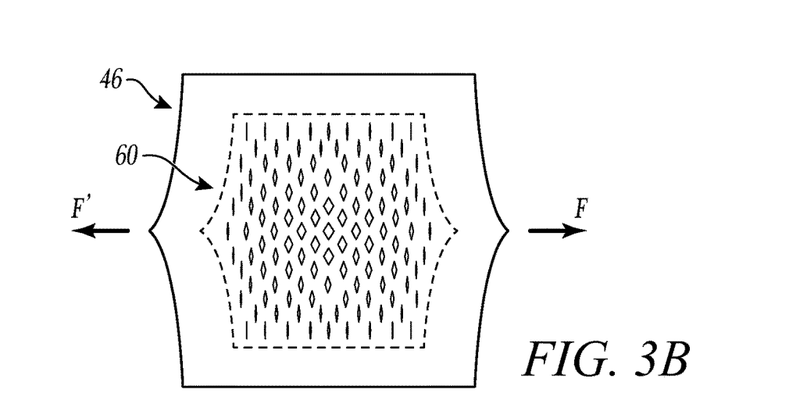
FIG. 3B is top elevational view of the body-facing surface of at least a portion of the absorbent core of FIG. 3A with transverse forces being applied thereto.

In some implementations, the absorbent core 46 includes at least a portion thereof having a proportion of slits. In one embodiment, the slits have a configuration such that at least a portion thereof extends along the longitudinal axis of the absorbent core 46. In another embodiment, the slits have a configuration such that at least a portion thereof extends along the transversal axis of the absorbent core 46. The slits can reversibly enlarge or shrink in size upon application of a stretching force and/or upon absorption of a liquid without removal of material from the absorbent core 46. In other words, a portion of the absorbent core 46 may include a dynamic heterogeneous slit size distribution which may vary in response to stretching force and/or upon absorption of a liquid. FIGS. 3A and 3B further illustrate a non-limiting example of this implementation. FIG. 3A shows an elevated plan view of the absorbent core 46 at a given time t including a portion 60 thereof having an initial state of slit size distribution. While the slits are shown in a configuration including longitudinal lines having an intercalating relationship to respective neighbour lines, a possible variant may include longitudinal lines having a substantially horizontal alignment with respective neighbour lines. FIG. 3B shows an elevated plan view of the absorbent core 46 at a given time t' with stretching forces F and F' being applied transversely to such portion 60. The heterogeneous slit size distribution at time t' can reversibly return to substantially the initial slit size distribution of time t shown in FIG. 3A upon discontinuation of the stretching forces F and F'. The person of skill will readily understand that in another variant a similar behavior can be obtained upon liquid absorption by the absorbent core 46 or via stretching forces being applied longitudinally or being applied as a combination of longitudinal and transverse forces, or a combination thereof. In some implementations, the slits are created in absorbent core 46 without removal of absorbent material.

In some implementations, the absorbent core 46 has a central width that exceeds 60 mm. As used herein, the expression "central width" refers to a specific area of a layer, such as the absorbent core which is determinable as follows. A reference point on the sample layer that is disposed beneath the center of the vaginal orifice, when worn, is located. A plane parallel to a transverse centerline thereof and 3.75 centimeters forward from the reference point in the direction of the wearer's mons pubis is located. Another plane parallel to a lateral centerline thereof and 5.0 centimeters rearward from the reference point in the direction of the wearer's buttocks is also located. The greatest flat-out, uncompressed, un-manipulated, lateral width of the sample layer between the two planes is the absorbent width of the sample layer. In a specific example, the central width of the absorbent system is about 65 mm.

In one embodiment, the absorbent core 46 is made of a foam material. In some implementations of this embodiment, the foam material is an open-cell foam material. As used herein, the expression "open-cell foam" refers to a foam material wherein the gas pockets connect with each other.

The absorbent core 46 is of high density and in a specific example has a density of greater than about 0.10 g/cc. Specifically, the absorbent layer 46 can have a density in the range of from about 0.08 g/cc to about 0.15 g/cc. For example, the absorbent layer 46 can have a density between about 0.10 g/cc to about 0.15 g/cc, between about 0.12 g/cc to about 0.15 g/cc, between about 0.10 g/cc and about 0.12 g/cc. The person of skill can readily select an absorbent core 46 having a suitable density without undue experimentation.

The absorbent core 46 can be prepared over a wide range of basis weights. The absorbent core 46 may have a basis weight in the range of from about 50 g/m$^2$ to about 225 g/m$^2$. In a specific example, the basis weight ranges from about 75 g/m$^2$ to about 125 g/m$^2$. In another specific example, the basis weight ranges from about 85 g/m$^2$ to about 120 g/m$^2$ and, more specifically, ranges from about 90 g/m$^2$ to about 115 g/m$^2$.

In a specific example, the absorbent core 46 is a foam material obtained from the 3M Company (St. Paul, Minn., USA). In some implementations of this embodiment, the absorbent core 46 may have a basis weight in the range of from about 175 g/m$^2$ to about 225 g/m$^2$. In a specific example, the basis weight ranges from about 185 g/m$^2$ to about 220 g/m$^2$. In another specific example, the basis weight ranges from about 200 g/m$^2$ to about 220 g/m$^2$ and, more specifically, ranges from about 204 g/m$^2$ to about 217 g/m$^2$.

In another specific example, the absorbent core 46 is a foam material obtained from the FXI Company (Media, Pa., USA). In some implementations of this embodiment, the absorbent core 46 may have a basis weight in the range of from about 50 g/m$^2$ to about 100 g/m$^2$. In a specific example, the basis weight ranges from about 55 g/m$^2$ to about 90 g/m$^2$. In another specific example, the basis weight ranges from about 60 g/m$^2$ to about 80 g/m$^2$ and, more specifically, ranges from about 60 g/m$^2$ to about 70 g/m$^2$. In some specific examples, the absorbent core 46 has a weight of about 65 g/m$^2$.

The person of skill can readily prepare an absorbent core 46 having a suitable basis weight without undue experimentation.

The absorbent core 46 has a thickness which can be of up to about 4.0 mm. For example, of up to 3.5 mm, or of up to 3.0 mm, and the like. In a specific example, the absorbent core 46 has a thickness which may vary from about 2.0 mm to about 4.0 mm, or from about 2.0 mm to about 3.5 mm, or from about 2.0 mm to about 3.0 mm, or from about 2.0 to about 2.5 mm, or from about 2.5 to about 3.5 mm, and the like. The person of skill can readily prepare an absorbent core 46 having a suitable thickness without undue experimentation.

Main Body—Absorbent System—Reinforcement Layer

The reinforcement layer 48 has a central width and a perimeter. In some implementations, reinforcement layer 48 has a central width that substantially overlaps with the central width of the absorbent core 46 and has a perimeter that substantially overlaps with the perimeter of the absorbent core 46.

In some implementations, reinforcement layer 48 has a central width that substantially overlaps with the central width of the absorbent core 46 and at least part of the perimeter of the absorbent core 46 substantially coincides with at least part of the perimeter of the reinforcement layer 48.

In some implementations, reinforcement layer 48 has a central width that is smaller than the central width of the absorbent core 46. In some example, at least part of the perimeter of the absorbent core 46 substantially coincides with at least part of the perimeter of the reinforcement layer 48. In this implementation, the front and rear most portions of perimeter of the absorbent core 46 coincide with the front and rear most portion of the perimeter of the reinforcement layer 48. In some other examples, the perimeter of the reinforcement layer 48 is smaller than the perimeter of the absorbent core 46.

For example, in some implementations, at least part of the perimeter of the reinforcement layer 48 lies within at least part of the perimeter of the absorbent core 46. In other words, the absorbent core 46 may have at least part of its perimeter which exceeds at least part of the perimeter of the reinforcement layer 48. For example, at least part of the perimeter of the reinforcement layer 48 may lie within about 30 mm from at least part of the perimeter of the absorbent core 46, in some cases, within about 25 mm, or within about 20 mm, or within about 15 mm, or within about 15 mm, or within about 10 mm, and the like. Additionally or alternatively, at least part of the perimeter of the reinforcement layer 48 may lie within about 7.5 mm from at least part of the perimeter of the absorbent core 46, in some cases within about 5.0 mm, or within about 2.5 mm, or within about 1.0 mm, and the like.

Reinforcement layer 48 is adjacent to barrier layer 50 on its garment-facing surface and bonded to absorbent core 46 on its body-facing surface.

In some implementations, the reinforcement layer 48 is a multi-layer laminate of fabric (e.g. non-woven material such as cellulose or fluff pulp, or the like)/superabsorbent/fabric (e.g. non-woven material such as cellulose or fluff pulp, or the like).

Superabsorbent polymers are well known in the art. For the purposes of the present disclosure, the term "superabsorbent polymer" (or "SAP") refers to materials which are capable of absorbing and retaining at least about 10 times their weight in body fluids under a 0.5 psi pressure. The superabsorbent polymer particles which can be suitable for use in the present disclosure may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles which can be suitable for use in the present disclosure are crosslinked polyacrylates, such as the product offered by Sumitomo Seika Chemicals Co., Ltd. Of Osaka, Japan, under the designation of SA60N Type II, and the product offered by Chemdal International, Inc. of Palatine, Ill., under the designation of 2100A.

In further implementations, the reinforcement layer 48 comprises an additional structural layer which is adjacent to the absorbent core 46 and which is bonded to the body-facing surface of the reinforcement layer 48 through its garment-facing surface. In a specific example, the additional structural layer is made of a polypropylene perforated sheet. In another example, the additional layer is made of polyester perforated sheet.

In some other implementations, the reinforcement layer 48 is made of airlaid SAP and fabric. The airlaid being in some examples made of cellulose fibers blended without water.

In some implementations, the reinforcement layer 48 may provide strength to the absorbent core 46. In particular, the reinforcement layer 48 may allow reducing the likelihood of tearing or breaking of the absorbent core upon deformation.

One embodiment of the reinforcement layer 48 particularly well suited for use in the sanitary napkin 20 has a basis weight of from about 60 $g/m^2$ to about 150 $g/m^2$. In a specific example, the basis weight ranges from about 70 $g/m^2$ to about 125 $g/m^2$. Preferably the basis weight ranges from about 74 $g/m^2$ to about 87 $g/m^2$. In a specific example, the reinforcement layer 48 has a weight of between about 74 $g/m^2$ to about 87 $g/m^2$. In another specific example, the reinforcement layer 48 has a weight of between about 100 $g/m^2$ to about 150 $g/m^2$. In some implementations of this embodiment, wherein the absorbent core 46 from 3M is used, the weight of the reinforcement layer 48 has a basis weight of from about 74 $g/m^2$ to about 90 $g/m^2$. In some implementations of this embodiment, wherein the absorbent core 46 from FXI is used, the weight of the reinforcement layer 48 has a basis weight of from about 100 $g/m^2$ to about 150 $g/m^2$, preferably about 125 $g/m^2$.

The thickness of the reinforcement layer 48 can vary from about 0.1 mm to about 1.0 mm. In a specific example, the thickness can be from about 0.1 mm to about 0.5 mm, or from about 0.1 to 0.25 mm, and the like.

The body-facing surface of the reinforcement layer 48 is maintained in contact with the garment-facing surface of absorbent core 46 by hot melt adhesive. In some implementations, the hot melt adhesive is applied by a method that commonly implies slot-die coating above room temperature, but it also is possible to have hot-melt roller coating; hot-melt metering-rod coating, etc.

In the implementations wherein the foam material from 3M is used as an absorbent core 46, the weight of the absorbent core 46 and the reinforcement layer 48 combined can be between about 275 $g/m^2$ to about 300 $g/m^2$, or between about 280 $g/m^2$ to 300 $g/m^2$, or between about 290 $g/m^2$ to about 300 $g/m^2$, or about 291 $g/m^2$.

In the implementations wherein the foam material from FXI is used as an absorbent core 46, the weight of the absorbent core 46 and the reinforcement layer 48 combined can be between about 150 $g/m^2$ to about 250 $g/m^2$, or between about 175 $g/m^2$ to 200 $g/m^2$, or between about 185 $g/m^2$ to about 195 $g/m^2$, or about 190 $g/m^2$.

A person skilled in the art will appreciate that the combined weight of the absorbent core 46 and the reinforcement layer 48 may vary without departing from the present disclosure.

Main Body—Barrier Layer

Underlying the absorbent system 44 is a barrier layer 50 comprising liquid-impervious film material so as to prevent liquid that is entrapped in the absorbent system 44 from leaking out of the sanitary napkin and staining the wearer's undergarment. The barrier layer 50 is made preferably of polyethylene.

The cover layer 42 and the barrier layer 50 are joined along their marginal portions so as to form an enclosure or flange seal that maintains the absorbent system 44 captive. The joint may be made by means of adhesives, heat-bonding, ultrasonic bonding, radio frequency sealing, mechanical crimping, and the like and combinations thereof. The peripheral seal line is shown in FIG. 1 by the reference numeral 52. In a specific implementation, the flange seal formed by the cover layer 42 and barrier layer 50 extends over at least about 1.0 cm from the main body 22. In a specific implementation, the flange seal formed by the cover layer 42 and barrier layer 50 extends over at least about 1.25 cm from the main body 22. In a specific implementation, the flange seal formed by the cover layer 42 and barrier layer 50 extends over at least about 1.5 cm from the main body 22. In a specific implementation, the flange seal formed by the cover layer 42 and barrier layer 50 extends over at least about 1.75 cm from the main body 22. In a specific implementation, the flange seal formed by the cover layer 42 and barrier layer 50 extends over at least about 2.0 cm from the main body 22. It is understood that the flanged seal formed by the cover layer 42 and barrier layer 50 extends over 2.0 cm in the flange or wing regions of the sanitary napkin 20.

Main Body—Flaps

The flaps 38 and 40 are preferably made as integral extensions of the cover layer 42 and the barrier layer 50. These integral extensions are joined to one another along their marginal seal portions by adhesives, heat-bonding, ultrasonic bonding, radio frequency sealing, mechanical crimping, and the like and combinations thereof. Most preferably, such joining is made at the same time the cover layer 42 and the barrier layer 50 are bonded to one another to enclose the absorbent system 44. Alternatively, the flaps may include absorbent material between the cover layer and the barrier layer extensions. Such absorbent material may be an extension of the absorbent core 46, the reinforcement layer 48 or both.

Adhesive System

Figure 6:
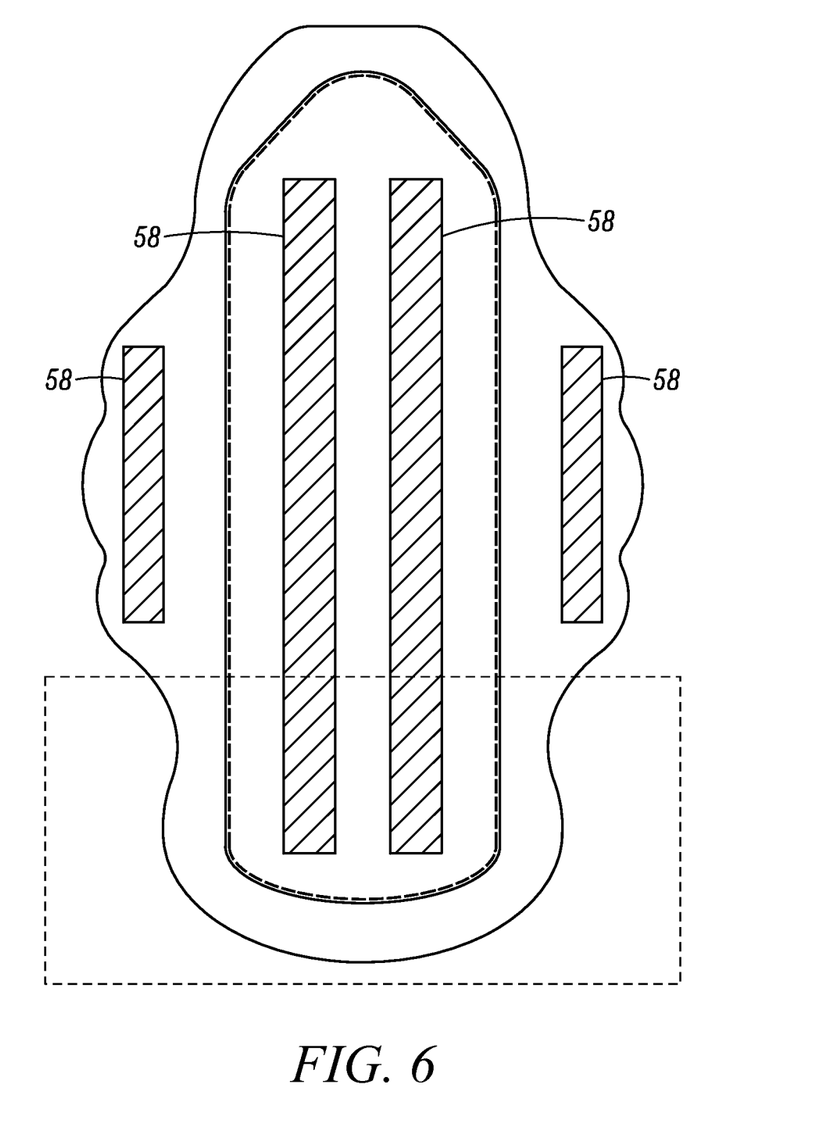
FIG. 6 is a top elevational view of the garment-facing surface of the sanitary napkin of FIG. 1 showing in dotted line the perimeter of the portion to be extracted from the sanitary napkin for determining the resiliency factor of the sanitary napkin and showing in shaded boxes the location of the adhesion system.

Referring to FIG. 6, in order to enhance the stability of the sanitary napkin, the garment-facing surface of the barrier layer 50 is provided with positioning adhesive material 58, typically hot-melt adhesive material capable of establishing a temporary bond with the undergarment material. A suitable material can be a synthetic rubber or polyolefin base hot melt adhesive. The positioning adhesive material 58 may be applied to the garment-facing surface of the barrier layer 50 in various patterns, including complete adhesive coverage, parallel longitudinal lines, a line of adhesive following the perimeter of the structure, transverse lines of adhesive or the like.

Standard release paper (not shown) covers the positioning adhesive 58 before the napkin is used to prevent the unwanted adherence of the napkin to itself or foreign objects. The release paper is of conventional construction (e.g. silicone coated wet-laid Kraft wood pulp) and suitable papers are available from Tekkote Corporation (Leonia, N.J., USA), and bear the designation FRASER 30#/61629. In a specific example, the weight of release paper used on the sanitary napkin 20 can be between about 30 g/m$^2$ and about 45 g/m$^2$, or between about 35 g/m$^2$ and about 40 g/m$^2$, or about 37 g/m$^2$.

Method of Manufacture

The above-described embodiment of the sanitary napkin 20 can be fabricated in a conventional manner in accordance with conventional techniques. Specifically, a laminate structure, sometimes referred to in the art as a web, is created. This laminate structure comprises an expanse of the materials from which the sanitary napkin will be created (i.e., the laminate structure comprises the following layers of material in a top-to-bottom order: an expanse of cover layer material; an expanse of absorbent core; an expanse of reinforcement layer; and finally an expanse of barrier layer).

Some of the materials are necessarily not continuous within the laminate structure, and where such is the case, they are positioned precisely, one with respect to another, in the relationship they will occupy in the final products. The cover layer material and the barrier layer material are then bonded together by applying pressure in the appropriate positions, and what will become the peripheral seal is created. The seal may also be made by means of heat-bonding, ultrasonic bonding, radio frequency sealing, mechanical crimping, and the like and combinations thereof. The sealed structure is then severed by conventional means (i.e., die-cutting, fluid-jet cutting, or by laser) from the web to create a discrete article.

The positioning adhesive material is then applied to the barrier layer and the flaps in the appropriate positions, and release paper is applied to cover the positioning adhesive. Alternatively, the positioning adhesive, or the positioning adhesive and the release paper may be applied to the web before the individual articles are severed therefrom.

In some specific examples, the adhesive is applied to the siliconed pouch and transferred to the barrier layer. For the flaps, the adhesive is applied to the silicone paper and transferred to the flaps.

As indicated earlier, the sanitary napkin 20 can have a thickness of up to about 5.0 mm. An apparatus suitable for measuring the thickness of the sanitary napkin can be a footed dial (thickness) gauge, available from Ames, with foot 0=30 mm, weight 102.5 g.

If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are folded on each side of the sample, prior to taking the thickness reading in the center of the sample.

The foot of the gauge is raised and the sample is placed on the anvil such that the foot of the gauge is approximately centered to the sample (or in the location of interest on the sample of interest). When lowering the foot, care is taken to avoid allowing the foot to "drop" or that undue force is not applied. The read out is allowed to stabilize for approximately 5 seconds. The thickness reading is then taken.

Resiliency Properties

A sanitary napkin in accordance with an embodiment of the present disclosure (e.g. sanitary napkin 20) may have resiliency properties that provide an ability of the sanitary napkin to return to its original shape after deformation. As used herein, the expression "resiliency properties" refers for example to the ability of the main body 22 of the sanitary napkin 20 to absorb energy when it is deformed and to release that energy upon unloading. In a specific implementation, the main body 22 initiates the return to its original shape substantially immediately after the forces causing the deformation are released. The longer it takes for the deformed main body 22 to initiate the return to its original shape, the lower should be its resiliency properties (low resiliency properties). The shorter it takes for the deformed main body 22 to initiate the return to its original shape, the higher should be its resiliency properties (high resiliency properties).

In some implementations, the resiliency properties of the main body 22 of the sanitary napkin 20 are provided at least by the absorbent system 44 including the absorbent core 46 and the reinforcement layer 48, the cover layer 22 and the barrier layer 50.

In some implementations, the resiliency properties of the main body 22 of the sanitary napkin 20 are provided at least by the absorbent system 44 including the absorbent core 46 and the reinforcement layer 48, the cover layer 22, the barrier layer 50 and the consistency of the width W of the main body 22 over at least at least 80% of the length of the main body.

In a specific implementation, the resiliency factor of a sanitary napkin according to embodiments of the present disclosure is of between about 15 to about 60, including any resiliency factor value or range therein. For example, the resiliency factor of a sanitary napkin according to embodiments of the present disclosure is of about 20, of about 25, of about 30, of about 35, of about 40, of about 45, of about 50, of about 55, and the like.

The resiliency factor of a sanitary napkin is determined as follows. Any wrapper wrapping the sanitary napkin is removed. The sanitary napkin is unfolded. Any adhesive release paper is removed from the sanitary napkin.

A portion of the absorbent product having a dimension of about 50-55 mm measured from the rear edge of the absorbent system towards the center of the sanitary napkin as shown in FIG. 6 is cut using means such as scissors or the like.

The thickness of the extracted portion is measured including the cover layer and the barrier layer using techniques and methods as defined herein.

The portions of the cover layer and of the barrier layer that extends on the lateral sides of the extracted portion are removed. This test is more concerned with the overall resiliency properties of the sanitary napkin and not merely the peripheral portions thereof.

Figure 7:
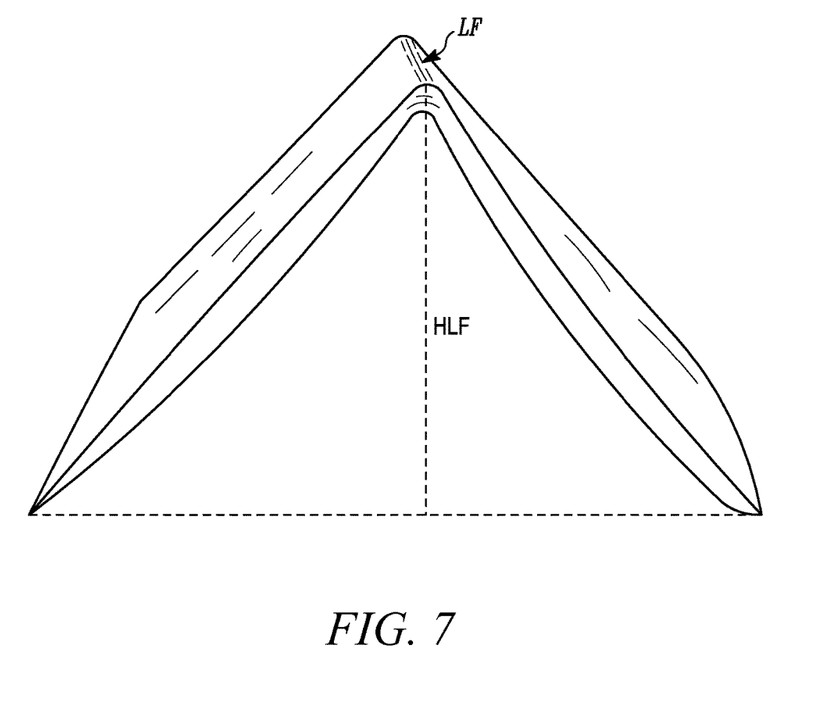
FIG. 7 is a side view of the extracted portion of the sanitary napkin of FIG. 6 in a "V"-shaped configuration.

The extracted portion is folded along the longitudinal axis L so as to form a "V"-shaped extracted portion having a longitudinal fold line LF so as to bring the cover layer of the portions extending on each side of the longitudinal axis L together (FIG. 7). Powder or another means of the sort is applied to the adhesive layer on the barrier layer to prevent premature or undesired adhesion of parts of the sanitary napkin together.

The "V"-shaped extracted portion is compressed using any conventional methods known in the art so as to apply about 1 kg of pressure on the "V"-shaped extracted portion for about 60 minutes. The pressure is released and the "V"-shaped extracted portion is allowed to unfold naturally. Powdering of the adhesive avoids adhesion of the "V"-shaped extracted portion to the compression means which would cause premature unfolding of the "V"-shaped extracted portion upon release of the compression means from the "V"-shaped extracted portion. The height of the longitudinal fold line LF (HLF) is measured after an about 30 second rest period (i.e., natural unfolding without external pressure or force), an about 2 minute rest period, and an about 5 minute rest period. To measure HLF, the "V"-shaped extracted product is placed on a flat surface as shown in FIG. 7, the "V"-shape facing downwards. The distance from the flat surface onto which the "V"-shaped extracted portion is placed to the longitudinal fold line (on the external surface of the material, i.e., the external surface of the "V"-shape) equals the height of the longitudinal fold line HLF.

The percent resiliency for each rest period is calculated from the initial thickness of the absorbent product over the height at the fold line (HLF). The resiliency factor represents the average of the combined percent resiliency results. Resiliency factors of sanitary napkins in accordance with the present disclosure and of sanitary napkins with zones of varying stiffness (prior art) are compared in Tables 1 and 2 below:

TABLE 1

| Resiliency properties | | | | |
|---|---|---|---|---|
| | Initial thickness (mm) | HLF after 30 sec. rest (mm) | HLF after 2 min. rest (mm) | HLF after 5 min. rest (mm) |
| Sanitary napkin with zones of varying stiffness (prior art) | | | | |
| Sample 1 | 2.7 | 14 | 9 | 7 |
| Sample 2 | 2.7 | 12 | 10 | 7 |
| Sample 3 | 2.8 | 12 | 7 | 5 |
| Sample 4 | 2.8 | 11 | 7 | 5 |
| Sample 5 | 2.8 | 13 | 8 | 5 |
| Average | 2.76 | 12.4 | 8.2 | 5.8 |
| % resiliency | | 22.3 | 33.7 | 47.6 |
| Resiliency Factor | | | 34.5 | |
| Sanitary napkin according to one embodiment of the present disclosure (absorbent core 46 obtained from 3M) | | | | |
| Sample 1 | 2.9 | 10 | 6 | 5 |
| Sample 2 | 3.1 | 10 | 6 | 5 |
| Sample 3 | 3.1 | 9 | 6 | 5 |
| Sample 4 | 2.9 | 8 | 5 | 5 |
| Sample 5 | 3 | 10 | 6 | 5 |
| Average | 3.0 | 9.4 | 5.8 | 5 |
| % resiliency | | 31.9 | 51.7 | 60 |
| Resiliency Factor | | | 47.8 | |

Tests performed under atmospheric conditions, i.e., temperature of about 25° C. and relative humidity of about 40%.

TABLE 2

| Resiliency properties | | | | |
|---|---|---|---|---|
| | Initial thickness (mm) | HLF after 30 sec. rest (mm) | HLF after 2 min. rest (mm) | HLF after 5 min. rest (mm) |
| Sanitary napkin with zones of varying stiffness (prior art) | | | | |
| Sample 1 | 3.1 | 14.0 | 10.0 | 8.0 |
| Sample 2 | 3.1 | 14.0 | 10.0 | 8.0 |
| Sample 3 | 3.1 | 14.0 | 10.0 | 9.0 |
| Sample 4 | 3.1 | 15.0 | 10.0 | 8.0 |
| Sample 5 | 3.1 | 15.0 | 11.0 | 9.0 |

TABLE 2-continued

Resiliency properties

| | Initial thickness (mm) | HLF after 30 sec. rest (mm) | HLF after 2 min. rest (mm) | HLF after 5 min. rest (mm) |
|---|---|---|---|---|
| Sample 6 | 3.0 | 14.0 | 10.0 | 7.0 |
| Sample 7 | 3.0 | 15.0 | 11.0 | 8.0 |
| Sample 8 | 3.0 | 15.0 | 10.0 | 7.0 |
| Sample 9 | 3.1 | 15.0 | 10.0 | 8.0 |
| Sample 10 | 3.1 | 15.0 | 11.0 | 8.0 |
| Average | 3.1 | 14.6 | 10.3 | 8.0 |
| % resiliency | | 21.0 | 29.8 | 38.4 |
| Resiliency factor | | | 29.7 | |
| Sanitary napkin according to one embodiment of the present disclosure | | | | |
| Sample 1 | 3.6 | 13.0 | 10.0 | 8.0 |
| Sample 2 | 3.6 | 10.0 | 8.0 | 7.0 |
| Sample 3 | 3.7 | 12.0 | 9.0 | 7.0 |
| Sample 4 | 3.6 | 12.0 | 8.0 | 7.0 |
| Sample 5 | 3.7 | 11.0 | 7.0 | 6.0 |
| Sample 6 | 4.1 | 14.0 | 10.0 | 9.0 |
| Sample 7 | 4.3 | 13.0 | 10.0 | 8.0 |
| Sample 8 | 4.0 | 12.0 | 9.0 | 8.0 |
| Sample 9 | 3.9 | 12.0 | 9.0 | 8.0 |
| Sample 10 | 4.1 | 14.0 | 10.0 | 8.0 |
| Average | 3.9 | 12.3 | 9.0 | 7.6 |
| % resiliency | | 31.4 | 42.9 | 50.8 |
| Resiliency factor | | | 41.7 | |

Flexibility Properties

A sanitary napkin in accordance with an embodiment of the present disclosure (e.g. sanitary napkin 20) may have flexibility properties that provide its ability to bend without breaking.

In a specific implementation, a sanitary napkin in accordance with an embodiment of the present disclosure (e.g. sanitary napkin 20) has flexibility properties under atmospheric conditions, i.e., temperature of about 25° C. and humidity of about 40%, with or without added liquid, of at least about 400 cN, or at least about 700 cN, or at least about 1000 cN, or at least about 1500 cN, or about 1600 cN. In comparison, a sanitary napkin having different zones of stiffness (prior art) showed a similar or a lower flexibility as measured according to the ASTM D 4032-82 CIRCULAR BEND PROCEDURE under varying conditions such as temperature, atmospheric humidity, added liquid to the napkin (about 4 ml of 0.9% saline), and the like.

The flexibility of a sanitary napkin may be measured by peakbending stiffness. Peak bending stiffness is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform which is 102.0 mm by 102.0 by 6.35 mm having an 18.75 mm diameter orifice. The lap edge of the orifice should be at a 45 degree angle to a depth of 4.75 mm;
2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;
3. A force-measurement gauge and more specifically an Instron inverted compression load cell. The load cell has a load range of from about 0.0 to about 2000.0 g;
4. An actuator and more specifically the Instron Model No. 1122 having an inverted compression load cell. The Instron 1122 is made by the Instron Engineering Corporation, Canton, Mass.

In order to perform the procedure for this test, as explained below, at least five representative sanitary napkins are necessary. From one of the at least five napkins to be tested, some number "Y" of 37.5 mm by 37.5 mm test specimens are cut. Specimens having portions in which a cover layer is joined directly to a barrier layer or which are a laminate of a cover layer, and a barrier layer without any component of the absorbent system, should not be tested. This test is more concerned with the overall flexibility of the sanitary napkin and not merely the peripheral portions thereof and, therefore, the flexibility of the present disclosure is more concerned with the flexibility of the absorbent portions of the sanitary napkin.

The test specimens should not be folded or bent by the test person, and the handling of specimens must be kept to a minimum and to the edges to avoid affecting flexural-resistance properties. From the four remaining sanitary napkins, an equal number "Y" of 37.5 mm by 37.5 mm specimens, identical to the specimens cut from the first napkin, are cut. Thus, the test person should have "Y" number of sets of at least 5 identical specimens.

The procedure for the CIRCULAR BEND PROCEDURE is as follows. The specimens are conditioned by leaving them at room temperature for a period of 1 hour or are conditioned by leaving them at 37° C. for a period of 1 hour. The test plate is leveled. The plunger speed is set at 50.0 cm per minute per full stroke length. A specimen is centered on the orifice platform below the plunger such that the cover layer of the specimen is facing the plunger and the barrier layer of the specimen is facing the platform. The indicator zero is checked and adjusted, if necessary. The plunger is actuated. Touching the specimen during the testing should be avoided. The maximum force reading to the nearest gram is recorded. The above steps are repeated until all said at least 5 of the identical specimens have been tested.

The peak bending stiffness for each specimen is the maximum force reading for that specimen. Remember that "Y" number of sets of at least five identical specimens were cut. Each set of said at least five identical specimens is tested and the at least five values received for that set are averaged. Thus, the test person now has an average value for each of the "Y" sets tested. The flexibility for a sanitary napkin is the average peak bending stiffnesses.

Softness Properties

A sanitary napkin in accordance with an embodiment of the present disclosure (e.g. sanitary napkin 20) may show enhanced softness properties in response to compression in the z-direction. As used herein, the expression "softness properties" refer to the properties of the sanitary napkin to be elastic and readily compressible in the z-direction. The softness properties of a sanitary napkin allow it to provide a soft and supple feeling to the wearer. The softness properties of the sanitary napkin are determined by obtaining the softness factor.

In a particular implementation, the sanitary napkin in accordance with an embodiment of the present disclosure has a softness factor of at least 0.15. For example, of between about 0.15 and about 0.30, or between about 0.15 and about 0.25, or between about 0.20 and about 0.23, or of a value of about 0.25, or of a value of about 0.21.

The softness factor of a sanitary napkin is determined as follows. Any wrapper wrapping the sanitary napkin is removed. The sanitary napkin is unfolded. Any adhesive release paper is removed from the sanitary napkin.

The thickness of the sanitary napkin is measured including the cover layer and the barrier layer. Powder or another means of the sort is applied to the adhesive layer on the barrier layer. Pressure is applied to the sanitary napkin (e.g. for 1 min) using conventional methods known in the art so as to decrease the thickness of the sanitary napkin by 20%. The softness factor corresponds to the pressure applied to the sanitary napkin to obtain a reduction of 20% in thickness.

The softness factor of sanitary napkins in accordance with embodiments of the present disclosure and of a sanitary napkin with zones of varying stiffness (prior art) are compared in the following Table 3:

TABLE 3

Softness Factor

|  | Sanitary napkin according to one embodiment of the present disclosure | Sanitary napkin with zones of varying stiffness (prior art) |
|---|---|---|
| Initial thickness | 2.8 mm | 2.8 mm |
| Final thickness | 2.2 mm | 2.2 mm |
| Pressure required to reduce thickness by 20% | 0.21 psi | 0.76 psi |
| Softness Factor | 0.21 | 0.76 |

|  | Sanitary napkin according to another embodiment of the present disclosure | Sanitary napkin with zones of varying stiffness (prior art) |
|---|---|---|
| Initial thickness | 3.0 mm | 2.7 mm |
| Final thickness | 2.4 mm | 2.1 mm |
| Pressure required to reduce thickness by 20% | 0.21 psi | 0.76 psi |
| Softness Factor | 0.21 | 0.76 |

The sanitary napkins having different zones of stiffness of (prior art) are not as soft and supple as sanitary napkins according to embodiments of the present disclosure.

Tensile Resistance

Tearing of a sanitary napkin or any parts thereof, such as the absorbent system, the cover layer or the barrier layer may occur upon placement of the sanitary napkin in the undergarment of the user or upon readjustment of the positioning of the sanitary napkin in the undergarment of the user. A sanitary napkin in accordance with an embodiment of the present disclosure (e.g. sanitary napkin 20) may show enhanced tensile resistance when subjected to longitudinal pulling forces and/or to transversal pulling forces.

Application of longitudinal and/or transversal pulling forces may initially cause tearing of the absorbent system. Tearing of the absorbent system may result in body fluids being immediately directed to the barrier layer, thereby increasing the discomfort and increasing the chances of leaking of the fluids out of the sanitary napkin.

Application of longitudinal and/or transversal pulling forces may further cause tearing of the cover layer and/or the barrier layer resulting in a sanitary napkin that is no longer useful for protection of the wearer's undergarment.

In some implementation, the enhanced resistance to tearing of the sanitary napkin in accordance with an embodiment of the present disclosure (e.g. sanitary napkin 20) is reflected with a resistance to a longitudinal force (longitudinal tensile resistance) of at least 3100 cN. For example, a resistance to a longitudinal force of between about 3100 cN and about 7500 cN, between about 3500 cN and about 4000 cN, between about 4500 cN and about 7500 cN, between about 5000 cN and about 7500 cN, between about 5250 cN and about 7500 cN, between about 5500 cN and about 7500 cN, between about 6000 cN and about 7500 cN, between about 6500 cN and about 7500 cN, and the like. Another example can be, for example, of at least about 3150 cN.

In addition or in the alternative, the enhanced resistance to tearing of the sanitary napkin in accordance with an embodiment of the present disclosure (e.g. sanitary napkin 20) is reflected with a resistance to a transversal force (transversal tensile resistance) of at least 2500 cN. For example, a resistance to a transversal force of between about 2500 cN and about 4575 cN, between about 3250 cN and about 4575 cN, between about 3500 cN and about 4575 cN, between about 3750 cN and about 4575 cN, between about 4000 cN and about 4575 cN, between about 4250 cN and about 4575 cN, between about 4500 cN and about 4575 cN, and the like. Another example can be, for example, of at least about 1450 cN.

In some other implementations, the enhanced resistance to tearing of the sanitary napkin in accordance with an embodiment of the present disclosure (e.g. sanitary napkin 20) is provided at least by the absorbent core 46.

In some other implementations, the enhanced resistance to tearing of the sanitary napkin in accordance with an embodiment of the present disclosure (e.g. sanitary napkin 20) is provided at least by the absorbent system 44 (i.e., the absorbent core 46 and the reinforcement layer 48).

In some other implementations, the enhanced resistance to tearing of the sanitary napkin in accordance with an embodiment of the present disclosure (e.g. sanitary napkin 20) is provided at least by the cover layer 42, the absorbent system 44 (i.e., the absorbent core 46 and the reinforcement layer 48) and the barrier layer 50.

In some other implementations, the enhanced resistance to tearing of the sanitary napkin in accordance with an embodiment of the present disclosure (e.g. sanitary napkin 20) is provided at least by the absorbent system 44 (i.e., the absorbent core 46 and the reinforcement layer 48) and the consistency of the width W of the absorbent.

In some other implementations, the enhanced resistance to tearing of the main body 22 of the sanitary napkin in accordance with an embodiment of the present disclosure (e.g. sanitary napkin 20) is provided at least by the absorbent system 44 (i.e., the absorbent core 46 and the reinforcement layer 48), the consistency of the width W of the absorbent system and the consistency of the thickness of the absorbent system 44.

In some other implementations, the consistency of the width W of the main body 22 improves the overall solidity of the sanitary napkin in accordance with an embodiment of the present disclosure (e.g. sanitary napkin 20) and its overall resistance at least to transversal pulling forces. In the specific implementation illustrated by sanitary napkin 20, the constant width W ensures that no significant zone of varying width is present on the main body 22 which would decrease the overall resistance of the sanitary napkin 20 to at least transversal pulling forces.

In some other implementations, the enhanced resistance to tearing of the main body 22 of sanitary napkin in accordance with an embodiment of the present disclosure (e.g. sanitary napkin 20) is provided at least by the absorbent system 44 (i.e., the absorbent core 46 and the reinforcement layer 48), the consistency of the width W of the absorbent system, the consistency of the thickness of the absorbent system 44 and the length of the portion of the flange seal extending from the main body. In this embodiment, the flange seal may provide elasticity in response to pulling forces which may improve the resistance to tearing.

In some other implementations, the enhanced resistance to tearing of the sanitary napkin in accordance with an embodiment of the present disclosure (e.g. sanitary napkin 20) is provided at least by the absorbent core 46.

In addition or in the alternative, the enhanced resistance to tearing of the sanitary napkin in accordance with an embodiment of the present disclosure (e.g. sanitary napkin 20) is provided at least by the absorbent core 46.

In some other implementations, the enhanced resistance to tearing of the sanitary napkin in accordance with an embodiment of the present disclosure (e.g. sanitary napkin 20) is provided at least by the absorbent system 44 (i.e., the absorbent core 46 and the reinforcement layer 48). In these implementations, the absorbent system 44 is able to resist a longitudinal force of between about 1400 cN and about 6000 cN, including any value or range therein. For example, the absorbent system 44 is able to resist a longitudinal force of between about 1550 cN and 6000 cN, of between about 2000 cN and about 6000 cN, of between about 3000 cN and about 6000 cN, of between about 4000 cN and about 6000 cN, of between about 4500 cN and about 6000 cN, of between about 5000 cN and about 6000 cN, of between about 5500 cN and about 6000 cN, and the like. In addition or in the alternative, the absorbent system 44 is able to resist a transversal force of between about 900 cN and about 4500 cN, including any value or range therein. For example, the absorbent system 44 is able to resist a transversal force of between about 1000 cN and about 4500 cN, between about 1500 cN and about 4500 cN, between about 2000 cN and about 4500 cN, between about 2500 cN and about 4500 cN, between about 3000 cN and about 4500 cN, between about 3250 cN and about 4500 cN, between about 3500 cN and about 4500 cN, between about 4000 cN and about 4500 cN, between about 4250 cN and about 4500 cN, and the like.

In some other implementations, the enhanced resistance to tearing of the sanitary napkin in accordance with an embodiment of the present disclosure (e.g. sanitary napkin 20) is provided at least by the cover layer 42, the absorbent system 44 (i.e., the absorbent core 46 and the reinforcement layer 48) and the barrier layer 50. In these implementations, the sanitary napkin 20 is able to resist a longitudinal force of between about 1400 cN and about 6000 cN, including any value or range therein. For example, the absorbent system 44 is able to resist a longitudinal force of between about 1550 cN and 6000 cN, of between about 2000 cN and about 6000 cN, of between about 3000 cN and about 6000 cN, of between about 4000 cN and about 6000 cN, of between about 4500 cN and about 6000 cN, of between about 5000 cN and about 6000 cN, of between about 5500 cN and about 6000 cN, and the like.

In addition or in the alternative, the enhanced resistance to tearing of the sanitary napkin in accordance with an embodiment of the present disclosure (e.g. sanitary napkin 20) is provided at least by the cover layer 42, the absorbent system 44 (i.e., the absorbent core 46 and the reinforcement layer 48) and the barrier layer 50. In these implementations, the sanitary napkin 20 is able to resist a transversal force of between about 900 cN and about 4500 cN, including any value or range therein. For example, the absorbent system 44 is able to resist a transversal force of between about 1000 cN and about 4500 cN, between about 1500 cN and about 4500 cN, between about 2000 cN and about 4500 cN, between about 2500 cN and about 4500 cN, between about 3000 cN and about 4500 cN, between about 3250 cN and about 4500 cN, between about 3500 cN and about 4500 cN, between about 4000 cN and about 4500 cN, between about 4250 cN and about 4500 cN, and the like.

Tensile resistance to longitudinal and transversal forces of sanitary napkins in accordance with embodiments of the present disclosure and of sanitary napkins with zones of varying stiffness (prior art) are compared in the Table 3 below:

TABLE 4

Tensile Resistance

| | Longitudinal Force (25 mm) (cN) | | Transversal Force (25 mm) (cN) | |
| --- | --- | --- | --- | --- |
| | Absorbent core + Reinforcement layer | Complete sanitary napkin | Absorbent core + Reinforcement layer | Complete sanitary napkin |
| one | 4871.7 | 5076.3 | 3558.9 | 4180.2 |
| embodiment | 4370.3 | 5391.5 | 3432.7 | 3919.4 |
| of the present | 4611.9 | 5193.3 | 2552.7 | 3907.2 |
| disclosure | 4415.8 | 5333.5 | 3343.7 | 3564.5 |
| | 4898.4 | 4795.8 | 3393.9 | 3756.0 |
| Average | 4776.8 | 5117.0 | 3244.3 | 4196.5 |
| Std-deviation | 4699.4 | 5657.4 | 3509.3 | 3957.0 |
| one | 5930.1 | 7125.7 | 4280.1 | 4560.5 |
| embodiment | 5953.8 | 6970.5 | 4436.3 | 4382.6 |
| of the present | 5617.0 | 7477.8 | 4114.4 | 3492.6 |
| disclosure | 5544.9 | 7409.7 | 3892.1 | 4342.5 |
| | 5718.5 | 6758.6 | 3700.9 | 4862.6 |
| Average | 5752.9 | 7148.5 | 4084.8 | 4328.2 |
| Std-deviation | 183.5 | 300.4 | 294.6 | 510.1 |

TABLE 4-continued

Tensile Resistance

| | Absorbent core | Complete sanitary napkin | Absorbent core | Complete sanitary napkin |
|---|---|---|---|---|
| prior art | 655.9 | 2009.4 | 689.9 | 1280.5 |
| | 722.5 | 2433.3 | 669.5 | 1287.8 |
| | 698.8 | 2069.0 | 733.1 | 1253.6 |
| | 626.8 | 2241.1 | 614.4 | 1250.2 |
| | 539.3 | 2107.6 | 708.7 | 1230.1 |
| Average | 648.7 | 2172.1 | 683.1 | 1260.4 |
| Std-deviation | 71.5 | 169.0 | 40.3 | 23.6 |
| prior art | 737.3 | 2355.6 | 737.3 | 2355.6 |
| | 440.8 | 2407.7 | 440.8 | 2407.7 |
| | 557.7 | 2523.8 | 557.7 | 2523.8 |
| | 781.6 | 2545.7 | 781.6 | 2545.7 |
| | 571.4 | 2292.6 | 571.4 | 2292.6 |
| Average | 617.8 | 2425.1 | 617.8 | 2425.1 |
| Std-deviation | 139.8 | 108.4 | 139.8 | 108.4 |

| | Absorbent core + Reinforcement layer | Complete sanitary napkin | Absorbent core + Reinforcement layer | Complete sanitary napkin |
|---|---|---|---|---|
| one | 4871.7 | 5076.3 | 3558.9 | 4180.2 |
| embodiment | 4370.3 | 5391.5 | 3432.7 | 3919.4 |
| of the present | 4611.9 | 5193.3 | 2552.7 | 3907.2 |
| disclosure | 4415.8 | 5333.5 | 3343.7 | 3564.5 |
| | 4898.4 | 4795.8 | 3393.9 | 3756.0 |
| | 4776.8 | 5117.0 | 3244.3 | 4196.5 |
| | 4699.4 | 5657.4 | 3509.3 | 3957.0 |
| | 4729.0 | 6063.0 | 3591.9 | 3930.3 |
| | 4657.5 | 6363.8 | 3450.8 | 3379.8 |
| | 4765.8 | 4970.5 | 4073.1 | 3460.5 |
| Average | 4679.7 | 5396.2 | 3415.1 | 3825.1 |
| Std-deviation | 174.7 | 496.2 | 376.2 | 281.3 |

| | Absorbent core | Complete sanitary napkin | Absorbent core | Complete sanitary napkin |
|---|---|---|---|---|
| prior art | 667.3 | 1948.3 | 573.5 | 1096.9 |
| | 615.2 | 1936.5 | 613.0 | 1026.7 |
| | 606.2 | 2124.4 | 527.9 | 938.7 |
| | 644.7 | 2206.3 | 422.5 | 1078.4 |
| | 633.3 | 1984.2 | 578.6 | 1099.5 |
| | 688.4 | 1969.5 | 702.8 | 1047.9 |
| | 598.2 | 2031.4 | 658.2 | 943.2 |
| | 645.2 | 2087.7 | 507.3 | 1049.4 |
| | 684.3 | 1992.7 | 545.9 | 1040.2 |
| | 665.1 | 1943.5 | 583.0 | 951.3 |
| Average | 644.8 | 2022.5 | 571.3 | 1027.2 |
| Std-deviation | 31.7 | 89.9 | 78.6 | 61.9 |

Tests performed under atmospheric conditions, i.e. temperature of about 25° C. and relative humidity of about 35%.

Sanitary napkins with zones of varying stiffness (prior art) showed less tensile resistance than sanitary napkins according to embodiments of the present disclosure.

ASTM D 624 may be used to measure the resistance to the formation of a tear (tear initiation) and the resistance to the expansion of a tear (tear propagation) of a sanitary napkin. Regardless of which of these two is being measured, a sanitary napkin sample—or the main body thereof or any parts thereof that is to be measured—is held between two holders and a uniform pulling force applied until the aforementioned deformation/tearing occurs. Sanitary napkins with low tensile resistance tend to have poor resistance to abrasion and when damaged will quickly fail and lose their absorption capacities.

Absorption Capacities

The maximum amount of liquid that a sanitary napkin may contain without applying pressure may be determined as follows. A sample sanitary napkin for which the absorption capacities are to be determined is first weighted to the nearest 0.01 g ($P_{dry}$). The sample sanitary napkin is placed in the container such that the article is totally submerged in 0.9% saline solution and is not bent or otherwise twisted or folded, and the cover layer is facing upwards. Soaking is performed for a period of at least about 10 minutes (for example 30 minutes). The sanitary napkin is then removed from the saline solution and hung vertically by pinching the sanitary napkin with a fold back clip without pinching the absorbent core. Hanging is performed for a period of at least about 1 minute. After that period, a measuring cup of known weight ($P_{empty\ cup}$) (e.g., to the nearest 0.01 g) is placed underneath the sample sanitary napkin, and the sample sanitary napkin is detached and allowed to drop into the cup. The weight of the cup and the sample napkin is then measured ($P_{total}$). The weight of the wet sanitary napkin ($P_{wet}$) is calculated by subtracting the weight of the empty cup ($P_{empty\ cup}$) from $P_{total}$. The absorption capacity of the sanitary napkin is determined as follows:

Absorption Capacity (grams)=$P_{wet}$−$P_{dry}$

The difference in grams is thus the absorption capacity. In some implementations, the sanitary napkin in accordance with embodiments of the present disclosure has an absorption capacity of between about 10.00 g and about 200.00 g, including any value or range therein. For example, the absorption capacity can be of at least about 10.00 g, of at least about 15.00 g, of at least 25.00 g, of at least 50.00 g, of at least 100.00 g, of at least 150.00 g, and the like. The person of skill will readily understand that the absorption capacity may be adjusted according to the intended use, for example a sanitary for day use may have an absorption capacity of between 80.00 g to about 100.00 g whereas a night use variant may have an increased absorption capacity of between 100.00 g and about 150.00 g.

Retention Capacities

The retention capacity of a sanitary napkin may be determined as follows. A sample sanitary napkin for which the retention capacity is to be determined is first weighted to the nearest 0.01 g ($P_{dry}$). The sample sanitary napkin is placed in a container such that the article is totally submerged in 0.9% saline solution and is not bent or otherwise twisted or folded, and the cover layer is facing upwards. Soaking is performed for a period of at least about 10 minutes (for example, 30 minutes). The sample sanitary napkin is then removed from the solution and placed into a spin dryer the barrier layer facing the exterior of the spin dryer. The spin dryer is spun for at least about 10 seconds (for example 60 seconds). The sample is removed and weighted ($P_{spun}$) (e.g., to the nearest 0.01 g). The retention capacity of the sanitary napkin is determined as follows:

Retention Capacity (grams)=$P_{spun}-P_{dry}$

The difference in grams is thus the retention capacity. In some implementations, the sanitary napkin in accordance with embodiments of the present disclosure has a retention capacity of between about 5 g and about 30 g, including any value or range therein. For example, the retention capacity can be of at least about 5.00 g, of at least about 10.00 g, of at least about 20.00 g, of at least about 25.00 g, and the like.

Applications of the product and methods of the present disclosure for sanitary and other health-care uses can be accomplished by any sanitary protection, incontinence, medical and absorbent methods and techniques as are presently or prospectively known to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth, and as follows in the scope of the appended claims.

Note that titles or subtitles may be used throughout the present disclosure for convenience of a reader, but in no way these should limit the scope of the disclosure. Moreover, certain theories may be proposed and disclosed herein; however, in no way they, whether they are right or wrong, should limit the scope of the disclosure so long as the disclosure is practiced according to the present disclosure without regard for any particular theory or scheme of action.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated. All documents mentioned in the specification are herein incorporated by reference in their entirety for all purposes.

The invention claimed is:

1. A sanitary napkin comprising:
   (a) a cover layer;
   (b) a barrier layer joined to the cover layer;
   (c) a main body comprising an absorbent system, the absorbent system being disposed between the cover layer and the barrier layer, wherein the absorbent system comprises:
      i. an absorbent core having an inner side that faces the barrier layer and an outer side that faces the cover layer; and
      ii. a reinforcement layer disposed between the inner side of the absorbent core and the barrier layer and having a basis weight of 60 g/m$^2$ to 150 g/m$^2$, the absorbent system having a consistent thickness throughout an entire extent of the absorbent system; and
   (d) flaps that project laterally outward from the main body,
   wherein the sanitary napkin has a resiliency factor of at least 15, a longitudinal tensile resistance of at least 3100 cN and a transversal tensile resistance of at least 2500 cN,
   the absorbent core has a perimeter and the reinforcement layer has a perimeter,
   the entire perimeter of the reinforcement layer overlaps and coincides with the entire perimeter of the absorbent core, and
   the main body has a width and a length, and the width is constant over at least 80% of the length of the main body.

2. A sanitary napkin as defined in claim 1, wherein the thickness of the sanitary napkin is of up to about 3.5 mm.

3. A sanitary napkin as defined in claim 1, wherein the resiliency factor is of at least about 20.

4. A sanitary napkin as defined in claim 1, wherein the longitudinal tensile resistance is of between about 5250 cN and about 7500 cN.

5. A sanitary napkin as defined in claim 1, wherein the transversal tensile resistance is of between about 3750 cN and about 4575 cN.

6. A sanitary napkin as defined in claim 1, having a softness factor of between about 0.15 and about 0.30.

7. A sanitary napkin as defined in claim 6, wherein the softness factor is about 0.21.

8. A sanitary napkin as defined in claim 1, having an absorption capacity of at least about 10.00 g.

9. A sanitary napkin as defined in claim 1, having a retention capacity of at least about 5.00 g.

10. A sanitary napkin as defined in claim 1, wherein said absorbent core includes a foam material.

11. A sanitary napkin as defined in claim 10, wherein the foam material is an open-cell foam material.

12. A sanitary napkin as defined in claim 1, wherein the reinforcement layer includes fabrics and superabsorbent materials.

13. A sanitary napkin as defined in claim 1, wherein the reinforcement layer includes polypropylene, fabrics and superabsorbent materials.

14. A sanitary napkin as defined in claim 1, wherein the reinforcement layer is a laminate of fabrics/superabsorbent materials/fabrics.

15. A sanitary napkin as defined in claim 1, wherein the reinforcement layer further includes a polypropylene perforated sheet.

16. A sanitary napkin as defined in claim 14, wherein the reinforcement layer further includes a polyester perforated sheet.

17. A sanitary napkin as defined in claim 1, wherein the absorbent system has a weight of between about 275 g/m$^2$ and about 300 g/m$^2$.

18. A sanitary napkin as defined in claim 1, wherein said absorbent system has a weight of between about 150 g/m$^2$ and about 250 g/m$^2$.

19. A sanitary napkin as defined in claim 1, wherein said sanitary napkin includes an adhesive material for retaining the sanitary napkin on an undergarment of a wearer.

20. The sanitary napkin of claim 1, wherein the absorbent core comprises a plurality of slits.

21. The sanitary napkin of claim 1, wherein the reinforcement layer is maintained in contact with the absorbent core by hot-melt adhesive.

22. A sanitary napkin comprising:
   (a) a cover layer;
   (b) a barrier layer joined to the cover layer;
   (c) a main body comprising an absorbent system, the absorbent system being disposed between the cover layer and the barrier layer, wherein the absorbent system comprises:
     i. an absorbent core having an inner side that faces the barrier layer and an outer side that faces the cover layer; and
     ii. a reinforcement layer disposed between the inner side of the absorbent core and the barrier layer and having a basis weight of 60 g/m$^2$ to 150 g/m$^2$, the absorbent system having a consistent thickness throughout an entire extent of the absorbent system; and
   (d) flaps that project laterally outward from the main body,
   wherein the sanitary napkin has a resiliency factor of at least 15, a longitudinal tensile resistance of at least 3150 cN and a transversal tensile resistance of at least 1450 cN,
   the absorbent core has a perimeter and the reinforcement layer has a perimeter,
   the entire perimeter of the reinforcement layer overlaps and coincides with the entire perimeter of the absorbent core, and
   the main body has a width and a length, and the width is constant over at least 80% of the length of the main body.

23. A sanitary napkin as defined in claim 22, wherein the absorbent system as a weight of between about 150 g/m$^2$ and about 250 g/m$^2$.

* * * * *